(12) United States Patent
Rotundo

(10) Patent No.: US 6,582,406 B2
(45) Date of Patent: Jun. 24, 2003

(54) DISPOSABLE SYRINGE

(75) Inventor: Giovanni Rotundo, Rome (IT)

(73) Assignee: Fada Italia, S.p.A., Rome (IT)

( * ) Notice: Subject to any disclaimer, the term of this patent is extended or adjusted under 35 U.S.C. 154(b) by 0 days.

(21) Appl. No.: 09/937,882

(22) PCT Filed: Feb. 2, 2001

(86) PCT No.: PCT/IB01/00294

§ 371 (c)(1),
(2), (4) Date: Jan. 15, 2002

(87) PCT Pub. No.: WO01/56632

PCT Pub. Date: Aug. 9, 2001

(65) Prior Publication Data

US 2002/0156429 A1 Oct. 24, 2002

(30) Foreign Application Priority Data

Feb. 2, 2000 (ES) ........................ 200000222 U

(51) Int. Cl.7 ................................. A61M 5/32
(52) U.S. Cl. ........................................ 604/192
(58) Field of Search ................................ 604/187, 192, 604/193, 194, 195, 196, 197, 198, 199

(56) References Cited

U.S. PATENT DOCUMENTS 4,961,730 A * 10/1990 Poncy ........................ 604/198
5,542,927 A * 8/1996 Thorne et al. ............... 604/110
5,593,391 A * 1/1997 Stanners ..................... 604/232

* cited by examiner

Primary Examiner—Michael J. Hayes
Assistant Examiner—Ann Y Lam
(74) Attorney, Agent, or Firm—Michael J. Striker

(57) ABSTRACT

An improved disposable syringe, made up of a cylindrical and hollow main body in which a piston can move that pushes the liquid to inject the same through a needle coupled to the front end of the main body, specifically to a neck established for this purpose in the same; the needle being complemented by a cone for coupling to said concetric neck provided at the front end of the main body; and the rear end to a protective sheath of the needle being, in turn, coupled by pressure to said cone in order to maintain sterilization of the needle.

11 Claims, 1 Drawing Sheet

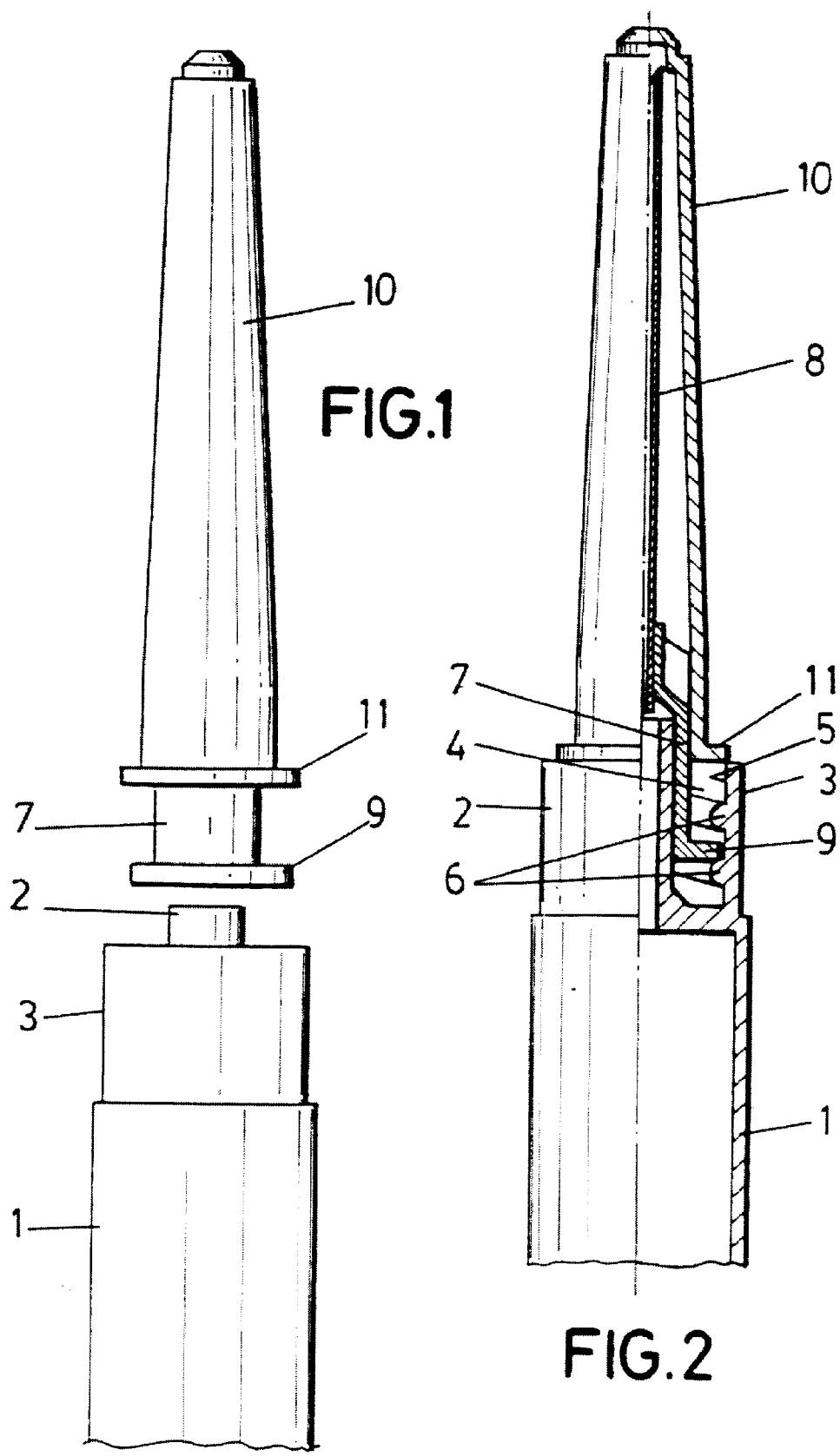

DISPOSABLE SYRINGE

OBJECT OF THE INVENTION

The invention refers to a disposable syringe that has been improved in determinate structural aspects with the object of achieving better performance and greater functional effectiveness than conventional syringes.

The object of the invention is to obtain a disposable syringe of the type comprising a main body in which the chamber for the liquid to be injected is determined, and a needle with a coupling cone on the end of said main body. The needle is complemented by a kind of sheath that protects and sterilises it. The syringe includes peculiarities with respect to the system for coupling the cone to the main body and coupling the protective sheath of the injection needle which, obviously, complements the assembly.

BACKGROUND OF THE INVENTION

There is a type of disposable syringe made up of a cylindrical, hollow body, which is open at its rear end to allow the movement of a rod corresponding to a piston that moves inside said cylindrical body for pushing and/or absorbing the liquid. The cylindrical body determines a chamber between its front end and the piston that can move axially in the same. Said axial rod ends in a kind of flattening or expansion to allow it to be manually actuated by the user.

This type of syringe is complemented by the corresponding needle which is housed in a covering in the form of a hood or sheath that constitutes a means for protecting the needle and also achieving hermetic sealing and the corresponding sterilisation, since the needle has a cone on its rear end for coupling to the corresponding end or neck established for this purpose on the front end of the main body of the syringe. The rear end of the sheath meets the perimeter of said coupling cone, thus achieving a hermetic seal and maintaining sterilisation of the needle, so that when the unit is going to be used, it is sufficient to couple the needle holder which slightly protrudes with respect to the rear end of the sheath over the neck of the body of the syringe, and then to extract or separate the sheath for the syringe to be ready to use.

As is clear, the coupling between the cone of the needle and the neck of the body of the syringe must be watertight to keep the liquid insulated inside the main body of the syringe, or what amounts to the same thing, in its corresponding chamber.

However, sometimes during handling, in the coupling and subsequent extraction of the protective sheath of the needle, a slight uncoupling and/or mobility of said cone occurs with respect to the neck of the body of the syringe, thus losing its hermetic seal and making it possible for air to enter the chamber, or even an unwanted exit of liquid.

When the protective sheath of the needle is being separated, it may also become badly aligned due to the tilting that may occur on the coupling cone, all of which means the risk of losing water-tightness of the liquid to be injected, or even problems of another kind with respect to the effectiveness and proper insertion of the needle in the muscular mass of the patient, as well as an irregular injection of liquid.

DESCRIPTION OF THE INVENTION

The syringe of the type referred to in the foregoing section, has a series of peculiarities on the basis of which the problems and drawbacks mentioned above are resolved.

More specifically, the first novel characteristic of the syringe of the invention is that the neck provided in the front end of the main body of the syringe, upon which the cone of the needle must be coupled, projects lengthwise with respect to the end in which the front end or part of the body extends, to define a large ring-shaped channel between said extension and the neck of the coupling. In said ring-shaped channel the rear end of the cone is housed, as well as the rear end of the sheath, although it is limited in its penetration in order to be able to separate it afterwards.

Another novel characteristic, is that the front extension of the main body of the syringe has an inner helicoidal fluting which determines a kind of thread for holding a ring-shaped rim provided in the rear part of the coupling cone. The latter thus remains completely held in place once it has been inserted into the concentric neck of the main body of the syringe, which makes it possible to extract and separate the sheath once the cone of the needle is coupled by pressure since, logically, to prevent the loss of water-tightness and therefore maintain sterilisation of the needle until it is to be used, the latter must be coupled to the body of the syringe with the sheath fitted and then finally extracted. Said sheath also includes a perimetric rear rim, which stops against the inner, slightly trunco-conical surface of the extension provided with the helicoidal fluting mentioned above, as the cone fits onto a complementary conical surface corresponding to the concentric neck of the main body. The liquid to be injected exits, pushed by the piston, through said neck and is injected by means of the needle that is coupled in the way described above.

In this way, an effective hermetic or watertight seal is achieved in the coupling of the cone to the body of the syringe, which will remain permanently intact since said cone is held in place by the inner fluting of the axial extension of the syringe's body, thus allowing the sheath to be extracted by pulling outwards without the coupling cone undergoing any movement or tilting during this operation of separation of the sheath.

DESCRIPTION OF THE DRAWINGS

To complement the description being given and in order to promote a fuller understanding of the features of the invention, in accordance with a preferred practical embodiment of the same, a set of drawings are attached as an integral part of said description, in which, illustratively and non-restrictively, the following is represented:

FIG. 1 shows an exploded view of the main body of the syringe that is the object of the invention, as well as of the assembly made up of the needle with its coupling cone and the protective sheath of the same.

FIG. 2 shows a view in longitudinal cross-section at ¼ of the syringe assembly, when the cone of the needle is coupled to the corresponding neck provided on the front end of the main body of the syringe, the sheath being in fitted position but ready for separation.

PREFERRED EMBODIMENT OF THE INVENTION

As may be observed in said drawings, the disposable syringe of the invention is made up of a main hollow cylindrical body, which is open at its rear end to allow the introduction of a piston for pushing the liquid to be injected. Between said piston and the front end of said main body the chamber for the liquid is established. Said front end of the main body (1) has an axial concentric neck (2) with a slightly trunco-conical shape while, externally to said neck (2), the body (1) has an extension (3) that is slightly shorter than the neck (2), a deep channel (4) being established between both of them. The wall (5) of said channel (4) converges downwards, that is, it defines an inverted conicality, with the peculiarity that in the surface of said inverted conical wall (5) a helicoidal fluting (6) is provided that determines a thread for effectively holding a cone (7) to carry the injection needle (8). Said cone (8) determines the means of coupling said needle to the main body of the syringe, with the peculiarity that said cone (7) has a perimetric rim or flattening (9) at its rear end which, when coupling or axial sliding on the neck occurs, causes a threading on the helicoidal fluting (6) of the inner conical surface (5) of the axial outer wall (3) of the body (1) of the syringe, thus fitting together the coupling cone (7) and the neck (2) of the body of the syringe by pressure, and therefore hermetically, and thus ensuring that the covering established by said body of the syringe (1) is watertight.

It is desirable that this type of needle (8) with its coupling cone (7) are complemented by a protective sheath (10) to maintain sterilisation and protection of the needle itself (8), which is coupled externally and by friction to the outer surface of the coupling cone (7). Therefore the separation of releasing of said sheath (10) is carried out once the cone (7) is coupled to the neck (2). In said coupling, logically and as may be observed in FIG. 2, the rear part, in which a flattening (11) of the sheath (10) is established, is housed in the channel (4) that determines the concentric neck (2) and the outer wall determined by the extension (3). The outer edge of said flattening (11) is stopped against the inner conical surface (5) of the wall (3), thus preventing, during said coupling, the sheath (10) from pressing excessively on the coupling cone (7), which allows the sheath (10) to be easily extracted once said cone (7) is coupled and held in place, without tilting, movement or loosening of the coupling cone (7) on the neck (2) of the syringe body (1) occurring during said operation.

What is claimed is:

1. A disposable syringe, comprising a substantially cylindrical hollow main body in which a piston is movable to push a liquid; said main body having a front end provided with a neck; a needle having a rear end facing said neck of said main body; a protective sheath removably arranged over said needle, said needle being provided with a conical element having one portion cooperating with said sheath so as to provide a hermetic sealing between said needle and said sheath and another portion cooperating with said neck of said main body so as to hold said needle in said main body.

2. A disposable syringe as defined in claim 1, wherein said neck of said main body has a radially inner wall and a radially outer wall which are spaced from one another so as to define a channel therebetween, said other portion of said conical element being inserted in said channel between said walls of said neck.

3. A disposable syringe as defined in claim 2, wherein said other portion of said conical element is located in said channel and engages with said outer wall of said neck of said main body.

4. A disposable syringe as defined in claim 3, wherein said other portion of said conical element has an engaging formation, said outer wall of said neck of said main body having an inner surface provided with a plurality of engaging formations with which said engaging formation of said conical element cooperates.

5. A disposable syringe as defined in claim 2, wherein said inner wall of said neck of said main body has a frusto-conical shape.

6. A disposable syringe as defined in claim 2, wherein said outer wall of said neck of said main body has a conical inner surface converging in a direction away from said needle.

7. A disposable syringe as defined in claim 3, wherein said other portion of said conical element has a radially inner surface abutting against said inner wall of said neck of said main body.

8. A disposable syringe as defined in claim 1, wherein said neck has a radially inner wall and a radially outer wall which are spaced from one another so as to form therebetween a channel in which said other portion of said conical element is introduced, said inner wall of said neck being conical and complimentary to said conical element, said inner wall of said neck having an outer conical surface which is complimentary to said conical element, while said outer wall of said neck has an inner surface which is also conical and engages with said other portion of said conical element.

9. A disposable syringe as defined in claim 8, wherein said sheath has a rear rim which has a size such that it can not be inserted into said channel between said inner and outer walls of said neck of said main body.

10. A disposable syringe, comprising a substantially cylindrical hollow main body in which a piston is movable to push a liquid; said main body having a front end provided with a neck; a needle having a rear end facing said neck of said main body; a protective sheath removably arranged over said needle, said needle being provided with a conical element having one portion cooperating with said sheath so as to provide a hermetic sealing between said needle and said sheath and another portion cooperating with said neck of said main body so as to hold said needle in said main body, said other portion fo said conical element having an inner surface abutting against an outer surface of said inner wall of said neck of said main body, and an outer surface abutting against an inner surface of said protective sheath, and also a radially outwardly extending formation cooperating with radially inwardly extending formations provided on an inner surface of said outer wall of said neck.

11. A disposable syringe as defined in claim 10, wherein said conical element being formed as a circumferentially closed element.

\* \* \* \* \*